United States Patent [19]
Wong et al.

[11] Patent Number: 4,693,895
[45] Date of Patent: Sep. 15, 1987

[54] COLON DELIVERY SYSTEM

[75] Inventors: Patrick S. L. Wong, Hayward; Felix Theeuwes, Los Altos, both of Calif.

[73] Assignee: ALZA Corporation, Palo Alto, Calif.

[21] Appl. No.: 665,279

[22] Filed: Oct. 26, 1984

[51] Int. Cl.$^4$ .................. A61K 27/12; A61K 9/24; A61K 9/36; A61M 31/00

[52] U.S. Cl. .................... 424/473; 424/469; 427/3; 428/507; 428/510; 604/890; 604/892

[58] Field of Search .......... 424/19, 473, 469; 604/890, 892; 427/3; 428/507, 510

[56] References Cited

U.S. PATENT DOCUMENTS

| | | | |
|---|---|---|---|
| 3,275,519 | 9/1966 | Glassman | 424/19 |
| 3,710,795 | 1/1973 | Higuchi et al. | 424/15 |
| 3,760,805 | 9/1973 | Higuchi | 424/15 |
| 3,926,188 | 12/1975 | Baker et al. | 424/19 |
| 4,093,708 | 6/1978 | Zaffaroni et al. | 424/15 |
| 4,116,241 | 9/1978 | Theeuwes et al. | 604/892 |
| 4,160,452 | 7/1979 | Theeuwes | 424/19 |
| 4,200,098 | 4/1980 | Ayer et al. | 604/892 |
| 4,278,738 | 7/1981 | Brax et al. | 428/515 |
| 4,309,996 | 1/1982 | Theeuwes | 604/892 |
| 4,326,525 | 4/1982 | Swanson et al. | 604/892 |
| 4,331,728 | 5/1982 | Theeuwes | 428/510 |
| 4,402,692 | 9/1983 | Takagishi et al. | 604/890 |
| 4,432,966 | 2/1984 | Zeitoun et al. | 424/21 |
| 4,449,983 | 5/1984 | Cortese et al. | 604/892 |
| 4,455,143 | 6/1984 | Theeuwes et al. | 604/890 |
| 4,475,916 | 10/1984 | Himmelstein | 604/890 |
| 4,483,846 | 11/1984 | Koide et al. | 604/890 |
| 4,522,625 | 6/1985 | Edgren | 424/19 |
| 4,595,583 | 6/1986 | Eckenhoff et al. | 424/15 |

FOREIGN PATENT DOCUMENTS

| | | | |
|---|---|---|---|
| 54-1392 | 1/1979 | Japan | 428/510 |
| 55-97953 | 7/1980 | Japan | 428/507 |

Primary Examiner—Ronald W. Griffin
Attorney, Agent, or Firm—Paul L. Sabatine; Edward L. Mandell; Steven F. Stone

[57] ABSTRACT

A drug delivery device is disclosed for delivering a drug by the oral route to the colon. The device comprises a laminated wall formed of three laminae surrounding a compartment contacting a drug with a passageway through the wall for dispensing the drug.

19 Claims, 11 Drawing Figures 4,693,895

COLON DELIVERY SYSTEM

FIELD OF THE INVENTION

The present invention pertains to the administration of a beneficially active agent to a preselected region of the gastrointestinal tract, specifically the colon. More particularly, the invention relates to both a novel and useful osmotic delivery system and method for delivering by the oral route a beneficial agent to the colon. The invention concerns also laminates useful for manufacturing the osmotic delivery system.

BACKGROUND OF THE INVENTION

A criticl and a continuous need exists for a delivery system for orally administering a beneficial agent in the colon. The oral delivery system is needed and it would be of a particular value in the management of ailments, diseases, or inflammation of the colon that require colon-targeted administration of a beneficially active agent. That is, the oral delivery system would have a therapeutic value where therapy indicates topical-colon administration of a beneficial agent to an affected colon site. A critical and a continuous need exists also for an oral delivery system that releases an active agent for systemic absorption of the active agent from the colon. The need for such a delivery system exists where it is therapeutically indicated to delay systemic absorption of the active agent for a predetermined period of time. More specifically, the need exists for a system that releases the active agent at about the time therapy is needed by a patient. An oral delivery system that releases an active agent for systemic absorption only in the colon at a preselected time would have a practical value in the management of patients with asthma, arthritis or inflammation. For example, the delivery system would be administered orally to the patient at bedtime with the system passing through the stomach and the intestine during the night and arriving at the colon, where it commences release in the colon of the active agent in the morning, thereby providing the patient with the desired therapy at the appropriate time.

Prior to this invention, tablets, capsules, and the like, were orally administered for dispensing an active agent throughout the gastrointestinal tract. However, for some agents a considerable amount of the active agent dispensed by the tablets and capsules is inactivated in the stomach because of the acidic and enzymatic environment of the stomach; additionally most of the agents are metabolized or absorbed in the small intestine from such immediate release forms. Consequently, very little of the active agent is available for producing a therapeutic result in the colon. The delivery of active agents through the rectum using suppositories or enemas often leads to colon therapy, but rectal administration is inconvenient and messy, and it is not readily accepted by the patient population.

It is immediately self-evident in view of the above presentation, that a need exists for an oral system that delays the onset of delivery for a period of time for the system to reach the colon. Such a period of time corresponds to the time required for the system to transit through the stomach and small intestine and commence delivery of the active agent about the time the system arrives at the colon.

OBJECTS OF THE INVENTION

It is an immediate object of this invention to provide a novel osmotic dispensing system for dispensing a useful agent to produce a beneficial effect, which dispensing system overcomes the aforesaid disadvantages associated with the prior art dispensing systems.

It is another object of this invention to provide an osmotic delivery system, for the controlled delivery of a beneficial agent to the colon, and which delivery system represents an advancement in colon-specific therapy.

It is another object of this invention to provide an oral, osmotic delivery system manufactured in the form of an osmotic device for dispensing a beneficial agent to the colon of the gastrointestinal tract of an animal for both topical and systemic therapy.

It is another object of this invention to provide an osmotic delivery system that delays the onset of agent release from the system for a period of time that approximately corresponds to the time required for the osmotic system to passes through the stomach and the small intestine.

It is another object of this invention to provide a delayed-release osmotic system useful for topical-colonic therapy by the oral route.

It is another object of this invention to provide a delayed-release osmotic system useful for releasing a drug in the colon for systemic absorption therefrom.

It is another object of this invention to provide an oral osmotic device comprising a compartment surrounded by a first wall formed of a semipermeable composition, and by a second wall formed of a fluid impermeable composition containing an osmotic solute with the device having an osmotic passageway through both walls.

It is another object of this invention to provide an osmotic device comprising a compartment surrounded by an inner wall formed of a semipermeable composition, a middle wall formed of a fluid impermeable composition containing an osmotic solute, an outer wall formed of an enteric composition, and a passageway through the walls for delivering a drug form the osmotic device.

It is another object of the invention to provide laminates useful for making osmotic delivery systems.

Other objects, features, aspects and advantages of this invention will be more apparent to those versed in the art from the following detailed specification taken in conjunction with the drawing figures and the accompanying claims.

BRIEF DESCRIPTION OF THE DRAWINGS

In the drawings, which are not drawn to scale, but are set forth to illustrate various embodiments of the invention, the drawing figures are as follows.

In the drawing figures and in the specification, like parts in related figures are identified by like parts. The terms appearing earlier in the specification and in the description of the drawing figures, as well as embodiments thereof, are further detailed elsewhere in the disclosure.

DETAILED DESCRIPTION OF THE DRAWINGS

Figure 1:
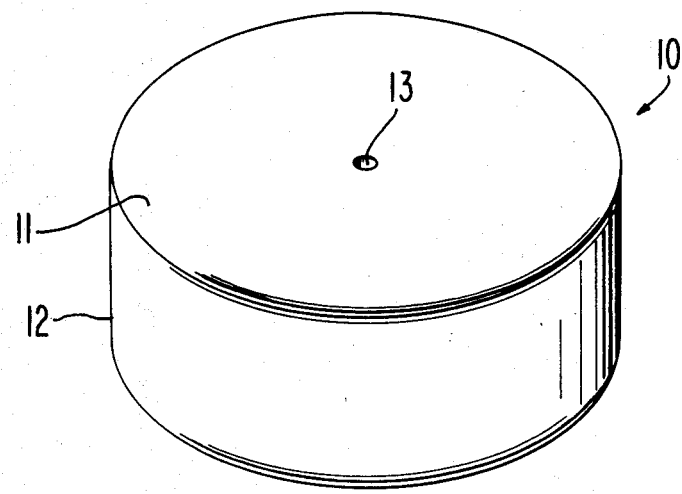
FIG. 1 is a view of an osmotic dispensing system designed for orally administering a beneficial agent such as a drug to the colonic region of the gastrointestinal tract.

Turning now to the drawings in detail, which drawings are examples of various osmotic delivery systems provided by the invention, and which examples are not to be construed as limiting, one example of an osmotic system is seen in FIG. 1, identified by the numeral 10. In FIG. 1, osmotic system 10 is designed as an orally administrable osmotic device, and it comprises a body member 11, a wall 12, and a passageway 13 in wall 12.

Figure 2:
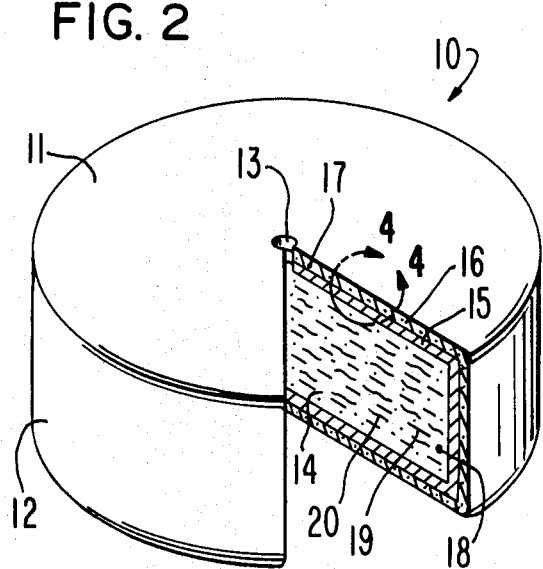
FIG. 2 is an opened view of the osmotic system of FIG. 1 depicting an embodiment of the invention comprising a laminated wall, which system is useful for delivering a beneficial agent to the colon.

In FIG. 2, osmotic system 10 is seen in opened section for illustrating the structural members of osmotic system 10. In FIG. 2, system 10 comprises body 11, wall 12, osmotic passageway 13 and internal compartment 14. Osmotic passageway 13 extends through wall 12 and it connects internal compartment 14 with the exterior of system 10. Wall 12 of the osmotic system illustrated in FIG. 2, comprises a laminate formed of two lamina, an inner lamina 15 and an outer lamina 16. Inner lamina 15 is adjacent to compartment 14, and outer lamina 16 is adjacent to the exterior of osmotic system 10, positioned distant from compartment 14. Lamina 15, as seen in FIG. 2, comprises a semi-permeable composition that is permeable to the passage of an external fluid present in the environment of use, and it is essentially impermeable to the passage of an active agent such as a drug. Lamina 15 is substantially inert, it maintains its physical and its chemical integrity during the dispensing of a beneficial drug, an it is non-toxic to animals, including humans. Lamina 15 is in laminar arrangement with lamina 16. Lamina 16 is made of a polymeric composition that is non-toxic, substantially non-erodible in the environment of use, it is substantially impermeable to the passage of a beneficial agent such as a drug, and it is moderately permeable to the passage of fluid present in the environment of use. Lamina 16 is made from a different polymeric composition than the composition forming lamina 15. Lamina 16 comprises further a plurality of discrete depots 17 containing an osmotic solute. The depots 17 of osmotic solute are dispersed throughout polymeric lamina 16 and the depots 17 are substantially surrounded and encapsulated by lamina 16 that binds depots 17 into a solid unit lamina 16. The polymer composition of lamina 16 surrounds depots 17 individually so that each depot 17 is encapsulated by a layer of polymer. The osmotic agent in depot 17 in a presently preferred embodiment is present as an osmotically effective solute, usually as the salt of said solute. The lamina 16 contains from 5 to 75%, by weight, of discrete deposits of 0.1 to 250 microns, surface area average diameter.

Compartment 14, in one embodiment, contains a beneficial agent 18, represented by dots, that is soluble to very soluble in an external fluid imbibed into compartment 14, and it exhibits an osmotic pressure gradient across laminated wall 12 against an external fluid 19, indicated by dashes, that is imbibed into compartment 14. In another embodiment, compartment 14 contains a beneficial agent 18 that has limited solubility in fluid 19 imbibed into compartment 14, and in this instance it exhibits a limited osmotic pressure gradient across wall 12, mainly semipermeable lamina 15 against the external fluid 19. In this latter embodiment, beneficial agent 18 optionally is mixed with an osmagent 20, indicated by wavy lines, that is soluble in the external fluid and it exhibits an osmotic pressure gradient across wall 12 against an external fluid.

Figure 3:
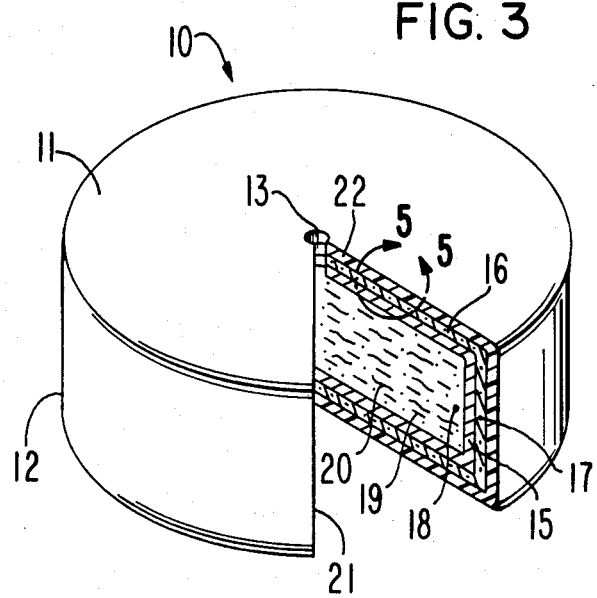
FIG. 3 is an opened view of the osmotic dispensing system of FIG. 1 illustrating an embodiment of the invention comprising a three-layered laminated wall, and which osmotic system is useful for delivering a beneficial agent to the colon.

FIG. 3 depicts another osmotic system 10 provided by the invention. In FIG. 33, system 10 is seen in opened section with a portion of wall 12 removed at 21. In FIG. 3, system 10 comprises body 11, wall 12, osmotic passageway 13, and internal compartment 14. Wall 12 of the osmotic system illustrated in FIG. 3 comprises a laminate formed initially of three lamina, an inner lamina 15, a middle lamina 16, and an outer lamina 22. Inner lamina 15 is adjacent to compartment 14 and outer lamina 22 faces the exterior of the system. Lamina 15 is formed of a semipermeable composition that is permeable to the passage of an external fluid and it is essentially impermeable to the passage of active agent 18. Lamina 15 is in contacting laminar arrangement with lamina 16. Lamina 16 comprises a polymeric composition substantially impermeable to the passage of a beneficial agent, and has a multiplicity of depots 17 of osmotic solute distributed therethrough. Lamina 22 is formed of an enteric material that does not dissolve or disintegrate in the stomach during the time the osmotic system remains in the stomach, and the enteric lamina should disintegrate once the osmotic system enters the small intestine. Compartment 14 of osmotic device 19 comprises a beneficial agent 18, and, optionally, an osmotically effective compound 19. During operation, when the osmotic system 10 is in the environment of use dispensing beneficial agent 18, osmotic compartment 14 contains also imbibed external fluid 20. Generally, wall 12 comprises a semipermeable lamina of 25 to 500 microns, an osmotic lamina of 25 to 300 microns, and an enteric lamina of 25 to 200 microns.

Figure 4:
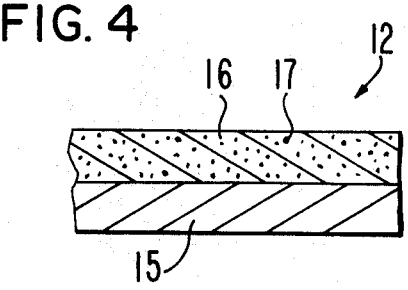
FIG. 4 illustrates a laminate defining the structural member of the osmotic system taken through 4—4 of FIG. 2; and, FIG. 5 illustrates a laminate defining the structural member of the osmotic device taken through 5—5 of FIG. 3.
Figure 5:
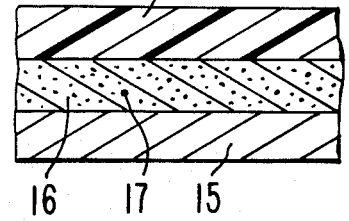

FIG. 4 illustrates a view taken through 4—4 of FIG. 2. FIG. 4 depicts wall 12 comprising semipermeable lamina 15 in laminar arrangement with osmotic lamina 16 having homogeneously or heterogeneously osmotic depots 17 dispersed throughout lamina 16. FIG. 5 illustrates a view taken through 5—5 of FIG. 3. FIG. 5 depicts wall 12 comprising three-layers in contacting, laminar arrangement. As illustrated, wall 12 comprises semipermeable lamina 15, osmotic lamina 16 with osmotic depots 17 and enteric lamina 22.

Osmotic delivery system 10 as seen in FIGS. 1 through 3 can be made into many embodiments for oral use for releasing locally or systemically acting therapeutic medicaments in the colon of the gastrointestinal tract. The oral system can have various conventional shapes and sizes such as round with a diameter of ⅛ inch to 9/16 inch, or it can be shaped like a capsule having a range of sizes from triple zero to zero and from 1 to 8.

In these manufactures, system 10 can be adapted for administering a beneficial agent to warm-blooded mammals such as humans.

DETAILED DESCRIPTION OF THE INVENTION

In accordance with the practice of this invention, semipermeable lamina 15 is formed of a material that does not adversely affect the beneficial agent, and the animal host. The semipermeable lamina-forming material is a polymer that is permeable to the passage of an external fluid such as water and aqueous biological fluids, while remaining substantially impermeable to beneficial agents and osmotic solutes. The selectively permeable materials forming semipermeable lamina 15 are materials that are insoluble in body fluids and they are non-erodible. Typical selective materials for forming lamina 15 include semipermeable polymers, also known to the art as osmosis membranes. The semipermeable polymers include cellulose acylate, cellulose diacylate, cellulose triacylate, cellulose ester, cellulose ether, and cellulose ester ether. Representative semipermeable polymers include cellulose acetate, cellulose diacetate, cellulose triacetate, dimethylcellulose acetate, cellulose acetate propionate, cellulose acetate butyrate, and the like. Semipermeable polymers are known in U.S. Pat. Nos. 3,173,876; 3,276,586; 3,541,005; 3,541,006; 3,546,142; 3,845,770; 3,916,899; 4,036,228; and 4,111,202.

Lamina 16, containing depots 17 of an osmotically effective solute, is formed of a polymer that surrounds and encloses depots 17 individually so that each depot 17 is encapsulated by a layer of polymer that forms lamina 16. The polymer used to form lamina 16 is substantially non-toxic, substantially non-erodible, impermeable to the passage of drug formulation, and it is moderately permeable to the passage of fluid present in the environment of use. In operation, when lamina 16 is in the fluid environment, fluid diffuses into polymeric lamina 16 and is imbibed into depots 17 dissolving the osmotic compound confined therein. The rate of fluid imbibition into depot 17 is related to the osmotic pressure gradient exhibited by the osmotic solute in depot 17 across the wall of depot 17 against the external fluid. As fluid is imbibed into depot 17, it continuously dissolves the solute and continuously fills depot 17, which solution formed therein generates a hydrostatic pressure in depot 17. This pressure is applied against the polymer wall causing it to rupture and form an aperture. The process is repeated during the period of time laimina 16 is exposed to fluid. As fluid is imbibed into the next depot it fills with solution and ruptures. The aperture formation is continuous, and by the inward progressive formation of apertures in lamina 16, a lattice or fluid channel is formed by contacting apertures through lamina 16. The channels provide a series of fluid paths for external fluid to flow through to semipermeable lamina 15, thus providing a source of fluid for the operation of semipermeable lamina 15.

Exemplary materials for fabricating lamina 16 include a member selected from the group consisting of poly(olefins), poly(vinyls), poly(ethylenes), poly(propylenes), poly(styrenes), poly(acrylonitriles), poly(vinylidene halides) and copolymers thereof. Typical materials for fabricating lamina 16 include a member selected from the group consisting of ethylene-vinyl ester copolymers having an ester content of 4 to 80% such as ethylene-vinyl acetate copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl-3-methylbutanoate copolymer, ethylene-vinyl-3-dimethyl butanoate copolymer, and ethylene-vinyl benzoate copolymer. Additional exemplary materials suitable for manufacturing lamina 16 include acrylonitrile-methyl vinyl ether, vinyl chloride-diethyl fumarate, plasticized poly(vinyl chloride), plasticized poly(amides), poly(isoprene), polymethylmethacrylate, poly(isobutylene), lightly cross-linked poly(vinyl pyrrolidone), vinyl-diethyl fumarate copolymer, ethylene-propylene copolymer, and the like. Solutes, as used for the present purpose are in a preferred embodiment salts and solutes in ion states that do not substantially diffuse through polymers; as reported in *Biological Sciences, Molecules to Man,* by Welch et al., pages 157 and 158, 1968, published by Houghton Mifflin Company, Boston. The polymeric materials are known in U.S. Pat. No. 4,190,642, and in *Handbook of Common Polymers,* by Scott et al., 1971, published by CRC Press, Cleveland.

Lamina 22 is made from an enteric materials that do not dissolve or disintegrate in the stomach during the period of time the osmotic system passes through the stomach. The enteric materials suitable for forming enteric lamina 22 include: (a) enteric materials that are digestible by enzymes in the small intestine; (b) enteric materials containing an ionizable polyacid; (c) enteric materials that are a long-chain polymer with an ionizable carboxyl group, and the like. Representative enteric materials include: (d) a member selected from the group consisting essentially of cellulose acetyl phthalate, cellulose diacetyl phthalate, cellulose triacetyl phthalate, cellulose acetate phthalate, hydroxypropylmethyl cellulose phthalade, sodium cellulose acetate phthalate, cellulose ester phthalate, cellulose ether phthalate, methyl cellulose phthalate, cellulose ester-ether phthalate, hydroxypropyl cellulose phthalate, and the like; (e) a member selected from the group consisting of keratin, keratin sandarac-tolu, salol, salol β-naphthyl benzoate and acetotannin, salol with balsam of Peru, salol with tolu, salol with gum mastic, salol and stearic acid, and salol and shellac; (f) a member selected from the group consisting of formalized protein, formalized gelatin, and formalized cross-linked gelatin and exchange resins; (g) a member selected from the group consisting of myristic acid-hydrogenated castor oil-cholesterol, stearic acid-mutton tallow, stearic acid-balsam of tolu, and stearic acid-castor oil; (h) a member selected from the group consisting of shellac, ammoniated shellac, ammoniated shellac-salol, shellac-wool fate, shellac-cetyl alcohol, shellac-stearic acid-balsam of tolu, and shellac-n-butyl stearate; (i) a member selected from the group consisting of abietic acid, methyl abietate, benzoin, balsam of tolu, sandarac, mastic with tolu, and mastic with cetyl alcohol; (j) a member selected from the group consisting of cellulose acetate with shellac, starch acetate phthalate, polyvinyl acid phthalate, 2-ethoxy-5-(2-hydroxyethoxymethyl)-cellulose phthalic acid, acid phthalates of carbohydrates, zein, alkyl resin-unsaturated fatty acids-shellac, colophony, mixtures of zein and carboxymethylcellulose; and the like. The enteric materials are discussed in *Remington's Pharmaceutical Sciences,* 13th Ed., pages 604 to 605, 1965, published by Mack Publishing Co., Eaton, Pa.

The osmotically effective compound, which is an osmotically effective solute, present in lamina 16 to form depots 17 include a member selected from the group consisting of water-soluble inorganic salts and water-soluble organic salts that are selected from the group consisting of magnesium sulfate, magnesium chloride, sodium chloride, lithium chloride, potassium sulfate, sodium carbonate, sodium sulfite, lethium sulfate, sodium sulfate, potassium acid phosphate, choline chloride, and the like. The osmotically effective solute can be used also as the osmotically effective solute 18 in compartment 14 for delivering drugs of limited aqueous solubility. The osmotically effective compounds are known to the art in U.S. Pat. Nos. 4,177,256 and 4,449,983.

The expression osmotic passageway as used herein comprises means and methods suitable for releasing a beneficial agent 18 from compartment 14. The osmotic passageway or orifice will pass through the laminated wall for communicating with compartment 14. The expression for passageway includes passageways formed by mechanical drilling or laser drilling through the laminated wall. Generally, for the purpose of the invention, the passageway will have a maximum cross-sectional area, A, defined by the equation $$(L/F) \times (Qv/t) \times (1/DS) \qquad (1)$$

wherein L is the length of the passageway (Qv/t) is the mass delivery rate of agent D released per unit time, D is the diffusion coefficient of the agent in the release solution, S is the solubility of the agent in the fluid and F has a value of approximately 2 to 1000, said osmotic passageway having a minimum area, $A_S$, defined by the equation $$\left[ \frac{Lv}{t} \times 8 \times \frac{\pi \eta}{\Delta P} \right]^{\frac{1}{2}} \qquad (2)$$

wherein L is the length of the passageway, v/t is the volume of the agent released per unit of time, is 3.14, is the viscosity of the solution being released, and P is the hydrostatic pressure difference between the inside and the outside of the compartment and having a value up to 20 atmospheres. The dimensions for the osmotic passageway is disclosed in U.S. Pat. No. 3,916,899.

The term beneficial agent as used in this specification and the accompanying claims includes drugs that are pharmacologically active, that produce, when released in the colon, a local or a systemic beneficial, therapeutic effect. The active drug that can be delivered includes inorganic and organic beneficially active compounds, such as materials that act on the nervous system, hypnotics, sedatives, physic energizers, tranquilizers, anticonvulsants, muscle relaxants, antiparkinson agents, analgesics, antiinflammatory, anesthetics, antimicrobials, antipyretics, and the like. The beneficial drugs are known to the medical art in *Pharmaceutical Sciences,* by Remington, 14th Ed., 1970, published by Mack Publishing Co., Easton, Pa.; in *American Drug Index,* 1976, published by J. B. Lippincott Co., Philadelphia, Pa.; in *The Drug, The Nurse, The Patient, Including Current Drug Handbook,* 1974–1976, by Falconer et al., published by Saunder Company, Philadelphia, Pa., and in *Medical Chemistry,* 3rd Ed., Vols. 1 and 2, by Burger, published by Wiley Interscience, New York.

The osmotic devices of the invention are manufactured as follows: In one embodiment, the drug is mixed with drug formulation ingredients by ballmilling, calendering, stirring, and pressing into a preselected shape having a shape that corresponds to the shape of the final osmotic device. The semipermeable material forming the first lamina can be applied by dipping, molding, or spraying the pressed mixture. One procedure for applying a wall-forming material is the air suspension procedure. The air suspension technique can be used for manufacturing a wall formed of a single layer, or formed of a multiplicity of layers. The air procedure is described in U.S. Pat. No. 2,799,241; in *J. Am. Pharm. Assoc.,* Vol. 48, pages 451 to 459, 1959, and in ibid, Vol. 49, pages 82 to 84, 1960. Procedures for measuring the surface area diameter of solutes are reported in *Journal Amer. Chem. Soc.,* Vol. 60, 309 to 319, 1938; *The Surface Chemistry of Solids,* by Gregg, 2nd Ed., 1961, published by Reinhold Corp., New York; *Absorption, Surface Area and Porosity,* by Gregg et al., 1967, published by Academic Press, New York; *Physical Absorption of Gases,* by Yound et al., 1962, published by Butterworth & Co., London; and *Fine Particle Measurements,* by Valla, 1959, published by Macmillan, New York. The osmotic pressure of solutes can be measured in a commercially available osmometer that measures the vapor pressure differences between pure water and the solution containing a solute to be analyzed, and according to standard thermodynamic principles, the vapor pressure ratio is converted into osmotic pressure difference. An osmometer that can be used for osmotic pressure measurements is identified as Model 302B, Vapor Pressure Osmometer, manufactured by the Hewlett Packard Co., Avondale, Pa. Procedures for measuring aperture formation in lamina 16 by osmotic solute generating hydrostatic pressure in depot 17 exceeding the cohesive integrity of the polymer with the formation of fluid channels can be determined by measurements predicated on pressure deflection and mechanical behavior measurement techniques are reported in *Modern Plastics,* Vol. 41, 143 to 144, 146 and 182, 1964; *Handbook of Common Polymers,* by Scott et al., 588 to 609, 1971, published by CRC Press, Cleveland, Ohio; *Machine Design,* 107 to 111, 1975; *J. Sci. Instruments,* Vol. 42, 591 to 596, 1965; and by measuring mechanical stress-strain patterns of polymers using the Instron ® Testing Machine, available from Instron Corp., Canton, Mass.; and by using the procedures disclosed in U.S. Pat. Nos. 4,177,256; 4,190,642; 4,298,003; and 4,265,874.

Exemplary solvents suitable for manufacturing the walls include inert inorganic and organic solvents that do not adversely harm the wall forming materials, the drug, the agent, and the final device. The solvents broadly include aqueous solvents, alcohols, ketones, esters, ethers, aliphatic hydrocarbons, halogenated solvents, cycloalphatic aromatics, heterocyclic solvents, and mixtures thereof. Typical solvents include acetate, ethyl acetate, methyl isobutyl ketone, n-hexane, ethylene glycol monoethyl acetate, carbon tetrachloride, methylene chloride, ethylene dichloride, propylene dichloride, cyclohexane, mixtures such as acetone and water, acetone and methanol, acetone and ethyl alcohol, methylene dichloride and methanol, ethylene dichloride and methanol, and mixtures thereof.

The following example is merely illustrative of the present invention, and it should not be considered as limiting the scope of the invention in any way, as this example and other equivalents thereof will become more apparent to those versed in the art in the light of the present disclosure, the drawings and the accompanying claims.

An oral osmotic device for the delivery of 5-aminosalicylic acid to the colon is made as follows: A drug composition is prepared for housing in the compartment of an osmotic device by thoroughly blending 200 mg of 5-amino salicylic acid, 20 mg of lactose, 10 mg of polyvinyl pyrrolidone, 20 mg of sodium chloride and 3 mg of magnesium stearate, and then compressing the homogeneous blend into a precompartment-forming drug formulation. Next, the compressed drug formulation is placed in an air suspension machine and coated with a semipermeable lamina-forming composition. The semipermeable lamina-forming composition comprises 80% by weight of cellulose acetate having an acetyl content of 39.8% and 20% by weight of cellulose acetate having an acetyl content of 32%. The semipermeable lamina is applied from a solvent mixture comprising methylene chloride and 95% ethanol, 80:20, wt:wt. The semipermeable lamina coated compartment is air dried in a forced air oven at 50° C. over night.

Next, a slurry of ethylene-vinyl acetate copolymer having a vinyl acetate content of 40% is prepared by mixing the copolymer in methylene chloride and adding thereto 35 g of sodium chloride. Then, the above-prepared semipermeable-limina coated compartment is submerged into the copolymer slurry and a layer of the copolymer containing the osmotic solute sodium chloride is coated onto the exterior surface of the semipermeable cellulose acetate. The laminated coated compartment is dried in a forced air oven at 50° C. for about 18 hours. Next, an enteric lamina is applied by placing the two-layered laminated-coated compartments into a pan containing shellac. The pan is prepared by pouring a quantity of shellac, U.S.P. grade, into a pan sufficient to thoroughly wet the entire surface of the ethylene-vinyl acetate copolymer. After the entire surface is coated with the shellac, the shellac coated drug compartments are removed from the pan and dried at 50° C. Then, the dry drug compartments again are placed in the pan, and more shellac is added to the pan, and another coating is applied to form the lamina. The three-layered compartments are dried in a forced air oven at 50° C. for one week. Then an osmotic passageway is laser drilled through the three laminae connecting the compartment with the exterior of the device. The osmotic passageway has a diameter of 9 mils for delivering the drug from the device.

Figure 6:
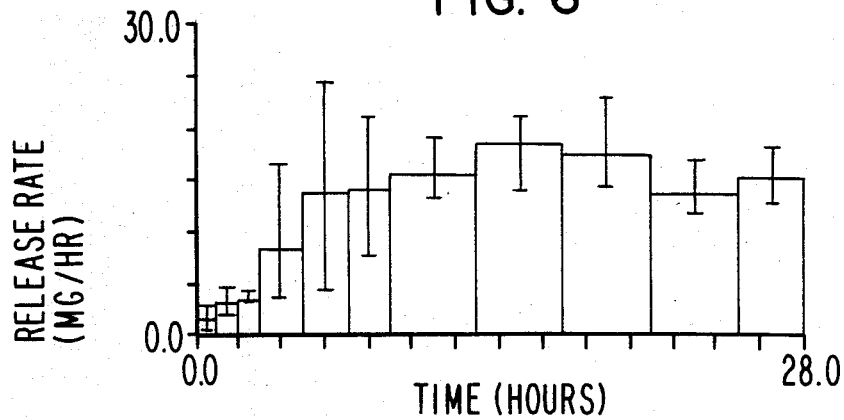
FIGS. 6, 8, and 10 depict the release rate in milligrams per hour of an active agent for a series of delivery devices provided by the invention; and, FIGS. 7, 9, and 11, depict the agent delivery start-up time for a series of delivery devices provided by the invention.
Figure 7:
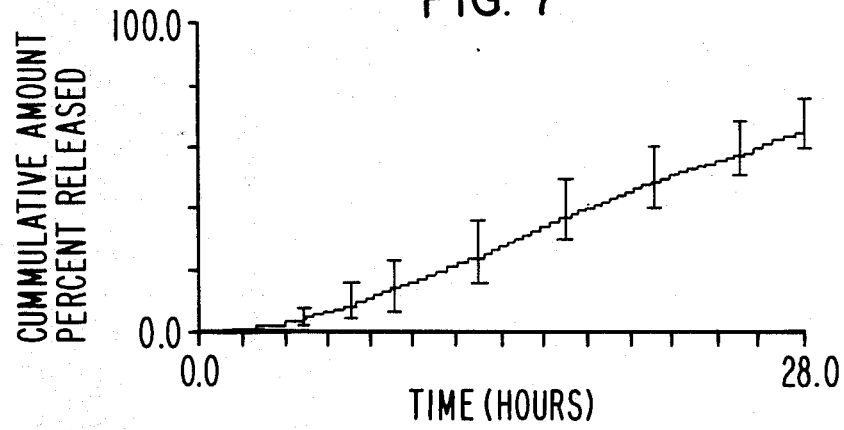

The above procedure is followed for preparing a series of drug delivery devices characterized by a delayed drug delivery start-up time. For example, one osmotic device is prepared having a compartment weighing 781.5 mg containing cimetidine hydrochloride consisting of cimetidine 76.5 wt % (weight percent) and HClH$_2$O 16.5 wt %, polyvinylpyrrolidone 4 wt %, sodium carboxymethylcellulose 2 wt %, and magnesium stearate 1 wt %. The semipermeable inner lamina weighs 47.8 by comprising 29.2 wt % cellulose acetate having an acetyl content of 32%, 30.8 wt % cellulose acetate having an acetyl content of 39.8%, 20 wt % cimetidine HClH$_2$O, 14 wt % hydroxypropyl methylcellulose, and 6 wt % polyethylene glycol 4000. The outer lamina weighs 28.4 mg and it consists of calcium sulfate 55 wt % and ethyl cellulose 45 wt %. The release rate for the device is depicted in FIG. 6. The device exhibits a 4-hour start-up as seen in FIG. 7. In the graphs, the bars represent the minimum and the maximum variation for the measurement at the indicated time.

Figure 8:
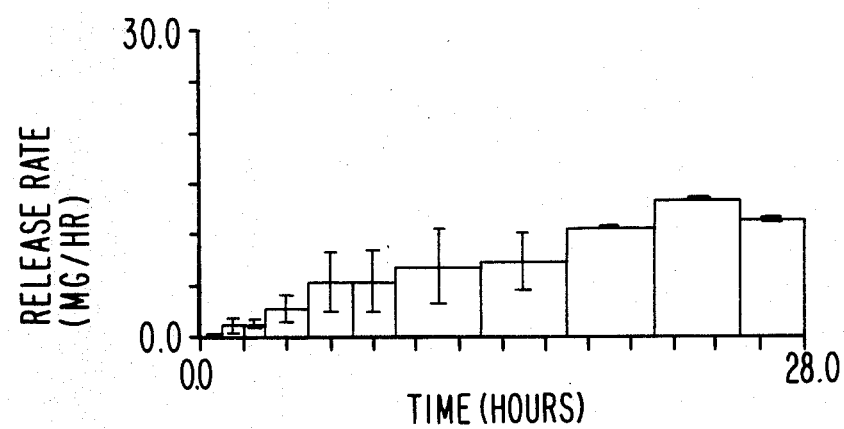
Figure 9:
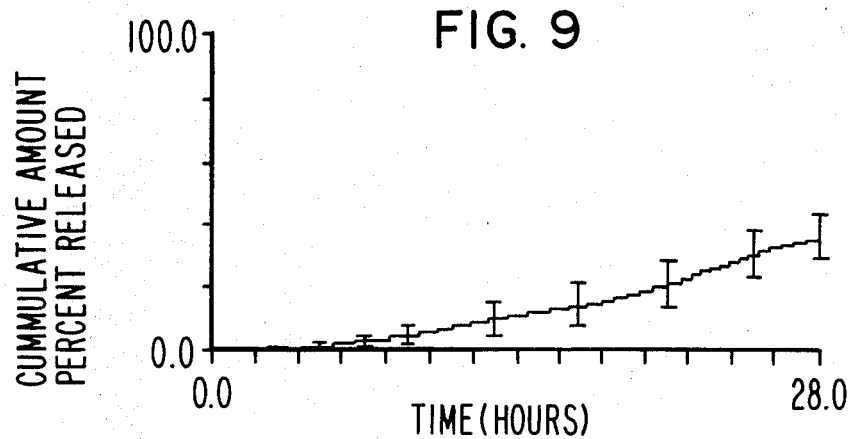

Another delivery device is prepared comprising a compartment weighing 781.5 mg containing cimetidine hydrochloride, consisting of cimetidine 76.5 wt % and HClH$_2$O 16.5 wt %, polyvinylpyrrolidone 4 wt %, sodium carboxymethylcellulose 2 wt %, and magnesium stearate 1 wt %. The inner, semipermeable lamina weighed 47.8 mg and it comprises 29.2 wt % cellulose acetate, having an acetyl content of 32%, 30.8 wt % cellulose acetate having an acetyl content of 39.8%, 20 wt % cimetidine HClH$_2$O, 14 wt % hydroxypropyl methylcellulose, and 6 wt % polyethylene glycol 4000. The outer lamina weighs 53.4 mg and it consists essentially of calcium sulfate 55 wt % and ethyl cellulose 45 wt %. The release rate for the delivery device is seen in FIG. 8. The device exhibits about an 8-hour start-up delivery time as seen in FIG. 9, as the outer lamina is approximately twice the thickness.

Figure 10:
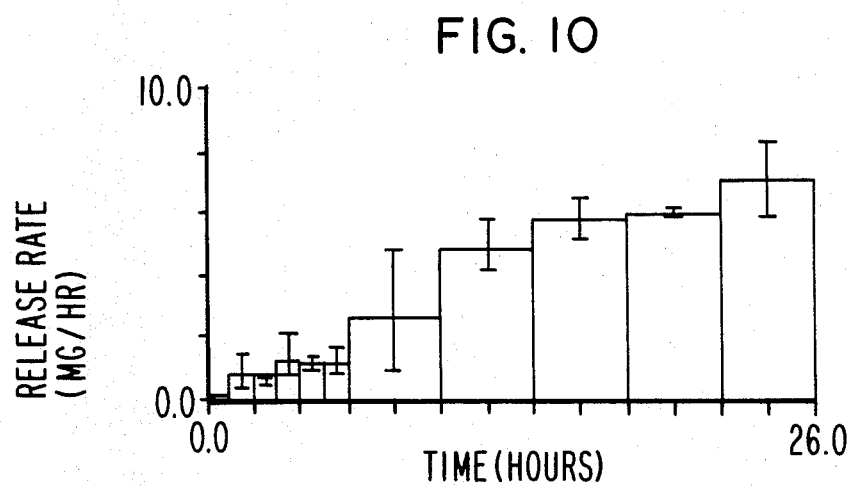
Figure 11:
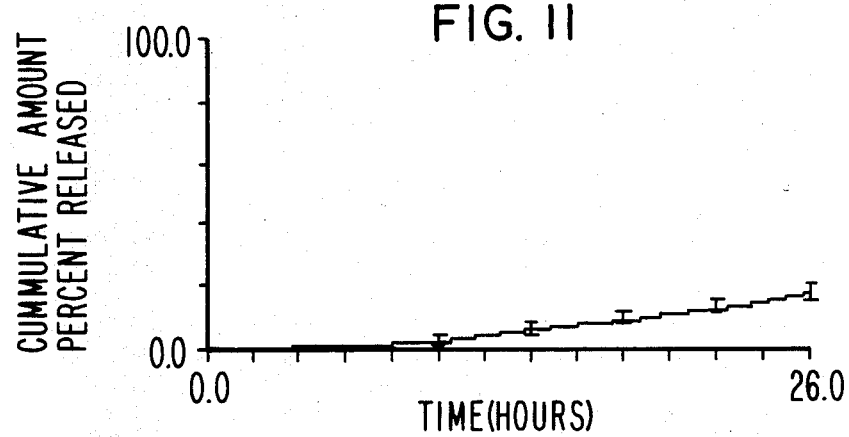

Another delivery device is manufactured comprising a compartment weighing 781.5 mg containing cimetidine hydrochloride consisting of cimetidine 76.5 wt % and HClH$_2$O 16.5 wt %, polyvinylpyrrolidine 4 wt %, sodium carboxymethylcellulose 2 wt % and magnesium stearate 1 wt %. The inner lamina facing the compartment weighs 47.8 mg and it comprises 29.2 wt % cellulose acetate having an acetyl content of 32%, 30.8 wt % cellulose acetate having an acetyl content of 39.8%, 20 wt % cimetidine HClH$_2$O, 14 wt % hydroxypropyl methylcellulose and 6 wt % polyethylene glycol 4000. The outer lamina weighs 23.6 mg and it consists of 20 wt % ethylene vinyl-acetate copolymer having a vinyl acetate content of 40%, 35 wt % ethyl cellulose and 45 wt % calcium sulfate. The release rate of the device is depicted in FIG. 10. The device exhibits a 10 hour start-up delivery time as seen in FIG. 11.

The novel osmotic systems of this invention use means for the obtainment of precise release rates in the environment of use while simultaneously maintaining the integrity and character of the system. While there has been described and pointed out features of the invention as applied to presently preferred embodiments, those skilled in the art will appreciate that various modifications, changes, additions and omissions in the systems illustrated and described can be made without departing from the spirit of the invention.

We claim:

1. An osmotic device for delivering a drug to a biological environment of use, said device comprising:
   (a) a shaped laminated wall comprising: (1) a first lamina comprising a semipermeable composition permeable to the passage of fluid and substantially impermeable to the passage of drug; (2) second lamina comprising a composition comprising a polymer and an osmotic solute, which polymer is permeable to the passage of fluid and impermeable to the passage of the osmotic solute; and (3) a third lamina comprising an enteric composition, said first, second and third lamina comprising different compositions with the laminated wall surrounding and defining:
   (b) a compartment containing a dosage unit amount of a beneficial drug formulation; and,
   (c) at least one passageway through the laminated wall communicating with the compartment and the exterior of the osmotic device for dispensing the drug formulation from the device to the environment of use.

2. The osmotic device for delivering a drug according to claim 1, wherein the biological environment of use is the gastrointestinal tract and the device is sized, shaped and adapted for oral administration into the gastrointestinal tract.

3. The osmotic device for delivering a drug according to claim 1, wherein the biological environment of use is the colon.

4. The osmotic device for delivering a drug according to claim 1, wherein the environment of use is the gastrointestinal tract, and when the device is in operation in the gastrointestinal tract, the third lamina erodes in the small intestine, a plurality of fluid paths are formed in the second lamina in situ, and fluid is imbibed through the first lamina into the compartment in a tendency towards osmotic equilibrium at a rate determined by the permeability of the first lamina and the osmotic pressure gradient across the first lamina, thereby forming a solution containing drug that is dispensed through the passageway from the device.

5. The osmotic device for delivering a drug according to claim 1, wherein the first lamina faces the compartment, and the third lamina faces the exterior of the device.

6. The osmotic device for delivering a drug according to claim 1, wherein the first lamina is formed of a member selected from the group consisting of cellulose acylate, cellulose diacylate, cellulose triacylate, cellulose acetate, cellulose diacetate, and cellulose triacetate.

7. The osmotic device for delivering a drug according to claim 1, wherein the third lamina is formed of a member selected from the group consisting of cellulose acetyl phthalate, cellulose diacetyl phthalate, cellulose triacetyl phthalate, cellulose acetate phthalate, hydroxypropylmethyl cellulose phthalate, sodium celluose acetate phthalate, methyl cellulose phthalate, and hydroxypropyl cellulose phthalate.

8. The osmotic device for delivering a drug according to claim 1, wherein the environment of use is the gastrointestinal tract, and wherein when the device is in operation in the gastrointestinal tract, the third lamina erodes in the small intestine and at least one path is formed in the second lamina which path is a passageway through the lamina for dispensing drug formulation to the environment of use.

9. The osmotic device for delivering a drug according to claim 1, wherein the first lamina is formed of a member selected from the group consisting of a cellulose ester, cellulose ether and cellulose ester ether.

10. The osmotic device for delivering a drug according to claim 1, wherein the third lamina is formed of a member selected from the group consisting of cellulose ester phthalate and cellulose ether phthalate.

11. An osmotic device for orally delivering a drug to the colon of an animal, said device comprising:
(a) a shaped laminated wall comprising: (1) an inner lamina comprising a semipermeable composition permeable to the passage of an external fluid and substantially impermeable to the passage of a beneficially active agent; and (2) an outer lamina composition comprising a polymer and an osmotically effective solute, said lamina permeable to fluid, impermeable to the passage of the osmotic solute, and substantially non-erodible and non-toxic in the presence of fluid, said inner lamina and outer lamina comprising different lamina composition which laminated wall surrounds and forms:
(b) a compartment;
(c) a dosage unit amount of a colon administrable drug formulation in the compartment; and,
(d) at least one passageway through the laminated wall connecting the exterior of the osmotic device with the compartment for delivering the drug formulation at a controlled rate to the colon.

12. The osmotic device for delivering a drug according to claim 11, wherein the inner lamina is formed of a member selected from the group consisting of cellulose acylate, cellulose diacylate, cellulose triacylate, cellulose acetate, cellulose diacetate, and cellulose triacetate.

13. The osmotic device for delivering a drug according to claim 11, wherein the outer lamina is formed of a member selected from the group consisting of a poly(olefin), poly(vinyl), poly(styrene), ethylene vinyl acetate copolymer, poly(acrylonitrile), ethyl cellulose and poly(vinylidene halide).

14. The osmotic device for delivering a drug to the colon of an animal according to claim 11, wherein at least one path is formed in the outer lamina, when the device is in operation in the colon, which path is a passageway through the lamina for dispensing drug formulation from the device.

15. The osmotic device for delivering a drug according to claim 11, wherein the inner lamina is formed of a member selected from the group consisting of a cellulose ester, cellulose ether, and cellulose ester ether.

16. A three-layered laminate useful for forming an osmotic drug delivery device, wherein the laminate comprises a first layer of a member selected from the group consisting of cellulose acylate, cellulose diacylate, and cellulose triacylate; a second layer comprising a member selected from the group consisting of a poly(olefin), poly(vinyl), ethylene vinyl acetate copolymer, poly(styrene), poly(acrylonitrile), ethyl cellulose and poly(vinylidene halide), and an osmotically effective compound dispersed in the second layer; and a third layer comprising a member selected from the group consisting of cellulose acetyl phthalate, cellulose diacetyl phthalate, and cellulose triacetyl phthalate.

17. A two-layered laminate useful for forming an osmotic drug delivery device, wherein the laminate comprises a first lamina consisting of a member selected from the group consisting of cellulose acylate, cellulose diacylate, and cellulose triacylate, and a second lamina consisting of a member selected from the group consisting of a poly(olefin), poly(vinyl), poly(styrene), ethylene vinyl acetate copolymer, poly(acrylonitrile), ethyl cellulose and poly(vinylidene halide), and which second lamina has dispersed therein an osmotically effective solute.

18. A three-layered laminate useful for forming an osmotic drug delivery device, wherein the laminate comprises a first layer of a member selected from the group consisting of a cellulose ester, cellulose ether and cellulose ester ether; a second layer of a member selected from the group consisting of a poly(olefin), poly(vinyl), ethylene vinyl acetate copolymer, poly(styrene), poly(acrylonitrile), ethyl cellulose and poly(vinylidene halide), said second layer comprising an osmotically effective solute dispersed therein; and a third layer comprising a member selected from the group consisting of cellulose ester phthalate, cellulose ether phthalate, and cellulose ester ether phthalate.

19. A two-layered laminate useful for manufacturing an osmotic drug delivery device, wherein the laminate comprises a first lamina consisting of a member selected from the group consisting of cellulose ester, cellulose ether and cellulose ester ether; and a second lamina consisting of a member selected from the group consisting of a poly(olefin), poly(vinyl), poly(styrene), ethylene vinylacetate copolymer, poly(acrylonitrile), ethyl cellulose and poly(isobutylene), and which second lamina has dispersed therein an osmotically effective solute.

* * * * *